United States Patent [19]

Wong et al.

[11] Patent Number: 5,766,887
[45] Date of Patent: Jun. 16, 1998

[54] SYNTHESIS OF 9-0-ACETYL N-ACETYLNEURAMINIC ACID OLIGOSACCHARIDES

[75] Inventors: Chi-Huey Wong, Rancho Santa Fe; Shuichi Takayama, San Diego, both of Calif.

[73] Assignee: The Scripps Research Institute, La Jolla, Calif.

[21] Appl. No.: 703,093

[22] Filed: Aug. 26, 1996

[51] Int. Cl.⁶ .................. C12P 19/44; C12P 19/26; C12N 9/24

[52] U.S. Cl. .................. 435/74; 435/84; 435/200; 435/201; 536/4.1; 536/17.2; 536/17.9

[58] Field of Search .................. 435/84, 74; 536/4.1, 536/17.2, 17.9

[56] References Cited

U.S. PATENT DOCUMENTS 5,461,143 10/1995 Wong.

OTHER PUBLICATIONS

Ritter, et al., "Biochemical and Serological Characteristics of Natural 9-0-Acetyl GD3 from Human Melanoma and Bovine Buttermilk and Chemically 0-Acetylated GD3". *Cancer Research*, 50:1403–1410 (1990).

*Primary Examiner*—Herbert J. Lilling
*Attorney, Agent, or Firm*—Donald G. Lewis

[57] ABSTRACT

Regioselective acetylation of the 9-hydroxyl group on N-acetylneuraminic acid is achieved enzymatically for producing oligosaccharides which contain a terminal N-acetylneuraminic acid moiety. This method provides access to O-acylated disialogangliosides as well as other N-acetyl-neuraminic acid oligosaccharides. These compounds are biologically and medicinally important and are difficult to obtain from nature or by chemical acylations. The methodology affords simple reaction conditions and minimal purification steps. In addition, the process affords good yields and the enzymes and reagents employed are commercially available with high stability and low costs.

8 Claims, 5 Drawing Sheets

1 R = H (N-Acetylneuraminic acid)
2 R = Ac (9-O-Acetyl N-acetylneuraminic acid)

3 R = H (GD3)
4 R = Ac (9-O-Acetyl GD3)

N-Acetylneuraminic acid moiety

SYNTHESIS OF 9-0-ACETYL N-ACETYLNEURAMINIC ACID OLIGOSACCHARIDES

GOVERNMENT RIGHTS

This invention was made with government support under Grant No. GM 44154 awarded by the National Institutes of Health. The U.S. government has certain rights in the invention.

DESCRIPTION

1. Field of the Invention

The invention relates to the enzymatic acetylation of carbohydrates. More particularly, the invention relates to the synthesis of the enzymatic preparation of 9-O-acetyl N-acetylneuraminic acid functionalized oligosaccharides through regioselective enzymatic acetylation of N-acetylneuraminic acid oligosaccharide precursors using Subtilisin and a commercially available acetate donor.

2. Background of the Invention

9-O-Acetyl N-acetylneuraminic acid (9-O-acetyl Neu5Ac, (2; FIG. 1) containing glycolipids and glycoproteins found on mammalian cells are important recognition elements involved in numerous biological events. In humans, 9-O-acetyl Neu5Ac (2; FIG. 1) itself is known as the recognition element that mediates influenza C virus attachment to cells (Rogers et al. *J. Biol. Chem.* 1986, 261, 5947). Recently, the disialoganglioside 9-O-acetyl GD3 (4, FIG. 1) which also contains a terminal 9-O-acetyl Neu5Ac moiety, has been reported as a malignant melanoma cell-specific antigen that is attractive as a target for immune intervention (Cheresh et al. *J. Biol. Chem.* 1984, 259, 7453).

The incidence of malignant melanoma has increased rapidly over the last decade. In 1992, in the United States alone, more than 32,000 individuals developed melanoma and 6,700 deaths from melanoma were recorded (Boring et al. *Cancer statistics* 1992, 42, 19). Though surgical treatment is fairly effective for small tumors in the early stages of this cancer, the 5-year survival rate after elective or therapeutic dissection drops to 25–35% for stage III patients (Coit et al. *Ann. Surg.* 1991, 214, 627). Recently, the importance of gangliosides as targets for passive and active specific immunotherapy has been documented by the clinical responses seen after treatment with anti-GD2 (Cheung et al. *J. Clin. Oncol.* 1987, 5, 1430; Irie et al. *Proc. Natl. Acad. Sci. USA* 1986, 83, 8694; Saleh et al. *Cancer Res.* 1992, 52, 4342), anti-GD3 (Houghton et al. *Proc. Natl. Acad. Sci. USA* 1985, 82, 1242), and anti-GM2mAb (Irie et al. *Lancet* 1989, I, 786), and by the correlation between antibody induction and improved prognosis after immunization with GM2 vaccines (Livingston et al. *Cancer Res.* 1989, 49, 7045; Livingston et al. *J. Clin. Oncol.* 1994, 12, 1036).

Among the various gangliosides expressed by malignant melanoma cells with a terminal 9-O-acetylneuraminic acid moiety is 9-O-acetyl GD3. This antigen is especially interesting in that it is found almost exclusively on malignant melanoma cells in adult humans and exhibits excellent availability for recognition by antibodies. 9-O-acetyl GD3 is therefore a specially attractive target for immune intervention (Cheresh et al. *J. Biol. Chem.* 1984, 259, 7453; Zhang et al. *Cancer Immunol. Immunother.* 1995, 40, 88; Hamilton et al. *Proc. Am. Assoc. Cancer Res.* 1993, 34, 491; Thurin et al. *J. Biol. Chem.* 1985, 260, 14556; Cheresh et al. *Science* 1984, 225, 844).

As such, procurement of sufficient amounts of pure 9-O-acetyl GD3 for the construction of vaccines and for further biological studies is very important. However, the 9-O-acetyl GD3 content of human melanoma tissues is low and there are no convenient natural sources for this acetylated disialoganglioside. Chemical acetylation of the more readily available GD3 has also been unsuccessful in providing the desired 9-O-acetyl GD3. This methodology acetylated the precursor GD3 using N-acetyl imidazole and pyridine and only provided GD3 acetylated at the subterminal sialic acid instead of at the desired terminal sialic acid (Ritter et al. *Cancer Res.* 1990, 50, 1403).

What is needed is an efficient synthetic method for producing industrial quantities of pure 9-O-acetyl GD3 and other 9-O-acetyl N-acetylneuraminic acid functionalized oligosaccharides from inexpensive commercially available precursors.

SUMMARY OF THE INVENTION

A new method for the regioselective acetylation of 9-O-acetyl N-acetylneuraminic acid analogs has been developed using Subtilisin and an acetate donor. The methodology is illustrated with the synthesis of 9-O-acetyl N-acetylneuraminic acid and 9-O-acetyl GD3 which are each regioselectively acetylated from N-acetylneuraminic acid based precursors. The method can be carried out in dimethylformamide to give the 9-O-acetylated product under mild conditions and high regioselectivity.

One aspect of the invention is directed to an enzymatic process for regioselectively acetylating an N-acetylneuraminic acid functionalized oligosaccharide. Preferred N-acetylneuraminic acid functionalized oligosaccharide include N-acetylneuraminic acid, disialoganglioside GD3, disialoganglioside GD2, disialoganglioside GD1a, disialoganglioside GD1b, monosialoganglioside GM1, tetrasialoganglioside GQ1b, trisialoganglioside GT1b, 3'-N-acetyl-neuramin-lactose, 6'-N-acetyl-neuramin-lactose, Sialyl Lewis X and CMP-Neu 5Ac.

The process comprises the step of reacting the N-acetylneuraminic acid functionalized oligosaccharide with an acetyl donor in an organic solvent in the presence of a protease for producing an 9-O-acetyl N-acetylneuraminic acid functionalized oligosaccharide. Preferred proteases include Subtilisin BPN', Subtilisin Carlsberg, Subtilisin 8350, Subtilisin 8397, and protease N. Preferred acetyl donors include vinyl acetate, isopropenyl acetate, trifluoroethyl acetate, trichloroethyl acetate, cyanomethyl acetate and acetoxime acetate. Preferred 9-O-acetyl N-acetylneuraminic acid functionalized oligosaccharides include 9-O-acetyl-N-acetylneuraminic acid, 9-O-acetyl-disialoganglioside-GD3, 9-O-acetyl-disialoganglioside GD2, 9-O-acetyl-disialoganglioside GD1a, 9-O-acetyl-disialoganglioside GD1b, 9-O-acetyl-monosialoganglioside GM1, 9-O-acetyl-tetrasialoganglioside GQ1b, 9-O-acetyl-trisialoganglioside GT1b, 9-O-acetyl-3'-N-acetyl-neuramin-lactose, 9-O-acetyl-6'-N-acetyl-neuramin-lactose, 9-O-acetyl-Sialyl Lewis X and CMP-9-O-Ac-Neu 5Ac. Preferred organic solvents include dimethylformamide, t-butanol, 1-pentanol, tetrahydrofuran, dioxanes, pyridine, benzene, toluene, acetone, diethyl ether, diisopropyl ether, ditertbutyl ether, chloroform, methylene chloride and mixtures of chloroform and methylene chloride with a solvent selected from the group consisting of dimethylformamide, t-butanol, 1-pentanol, tetrahydrofuran, dioxanes, pyridine, toluene, acetone, diethyl ether, diisopropyl ether, ditertbutyl ether.

Figure 1:
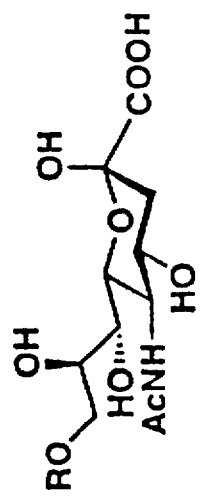
FIG. 1 shows the chemical structures of N-acetylneuraminic acid (1), 9-O-acetyl-N- acetylneuraminic acid (2), GD3 (3) and 9-O-acetyl-GD3 (4). The GD3 molecule contains an N-acetylneuraminic acid moiety on one of its terminal ends (bracketed area).
Figure 1:
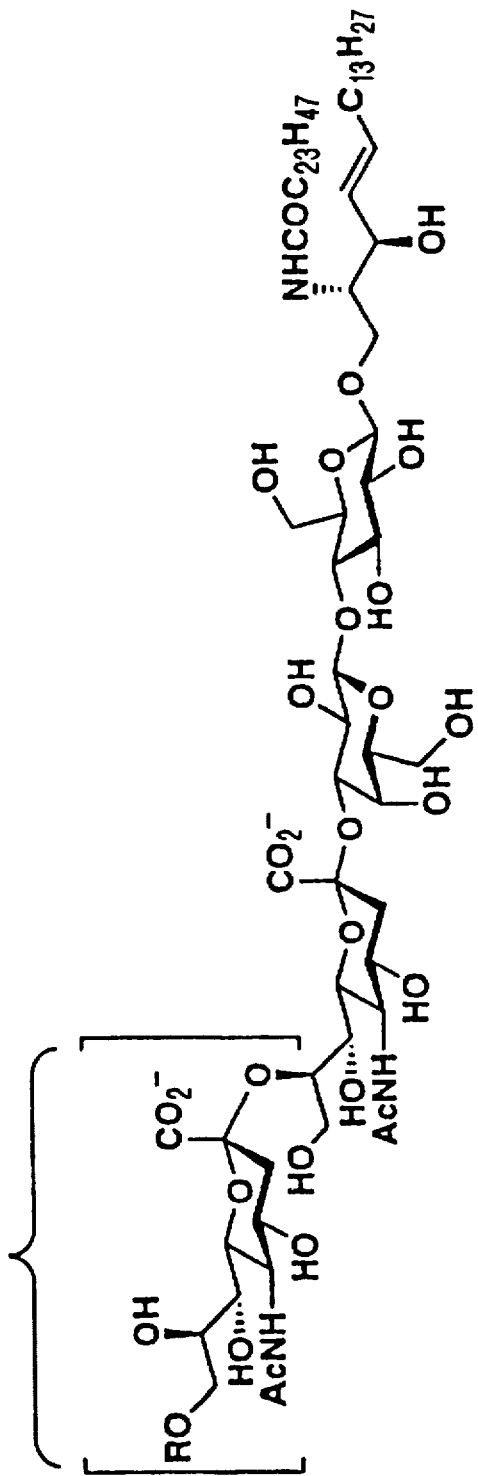
Figure 2A:
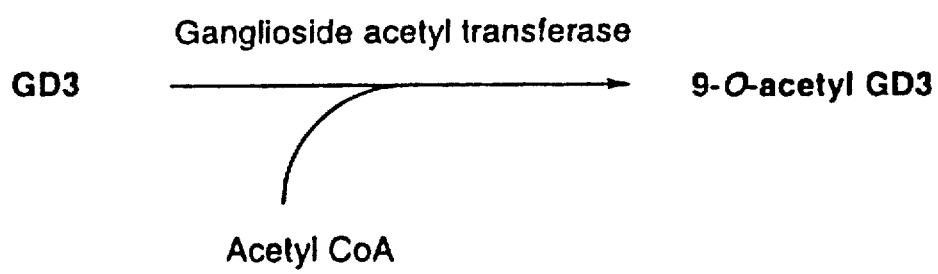
Figure 2B:
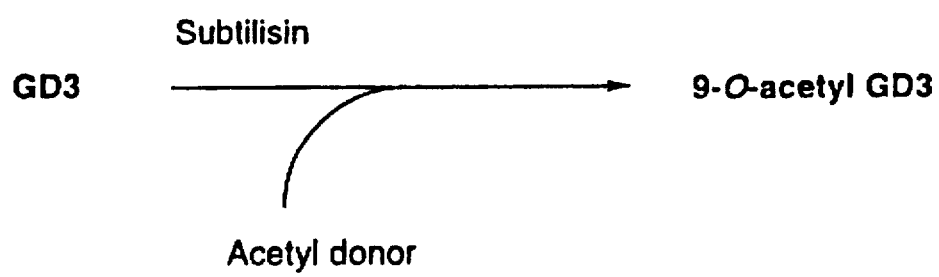

FIG. 2 illustrates enzyme-catalyzed regioselective acetylation of GD3 to produce 9-O-acetyl GD3 via (a) in vivo use of ganglioside O-acetyl transferase with acetyl-coenzyme A as the donor (b) in vitro use of subtilisin with a simple acetyl donor (eg. vinyl acetate).

Figure 3:
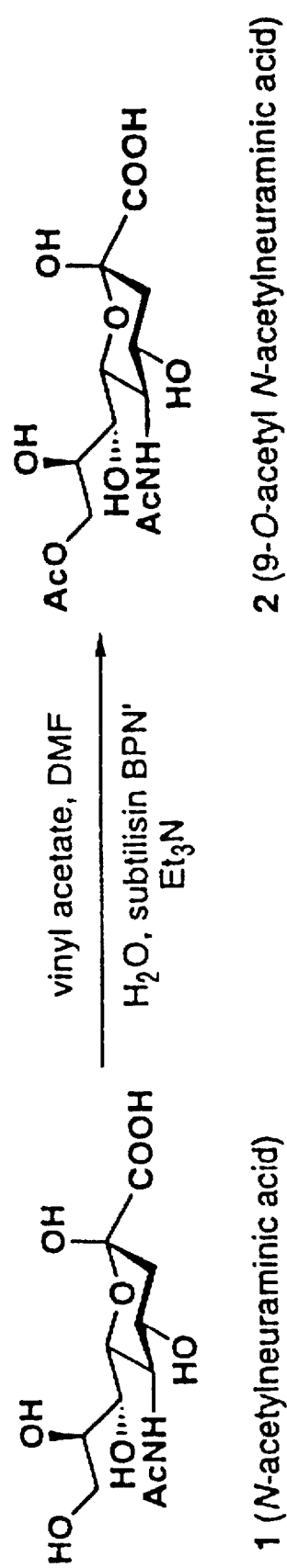

FIG. 3 illustrates enzymatic-catalyzed regioselective acetylation of N-acetylneuraminic acid (1) using subtilisin BPN' with vinyl acetate, triethylamine, in dimethylformamide (DMF) to form 9-O-acetyl-N-acetylneuraminic acid (2).

Figure 4:
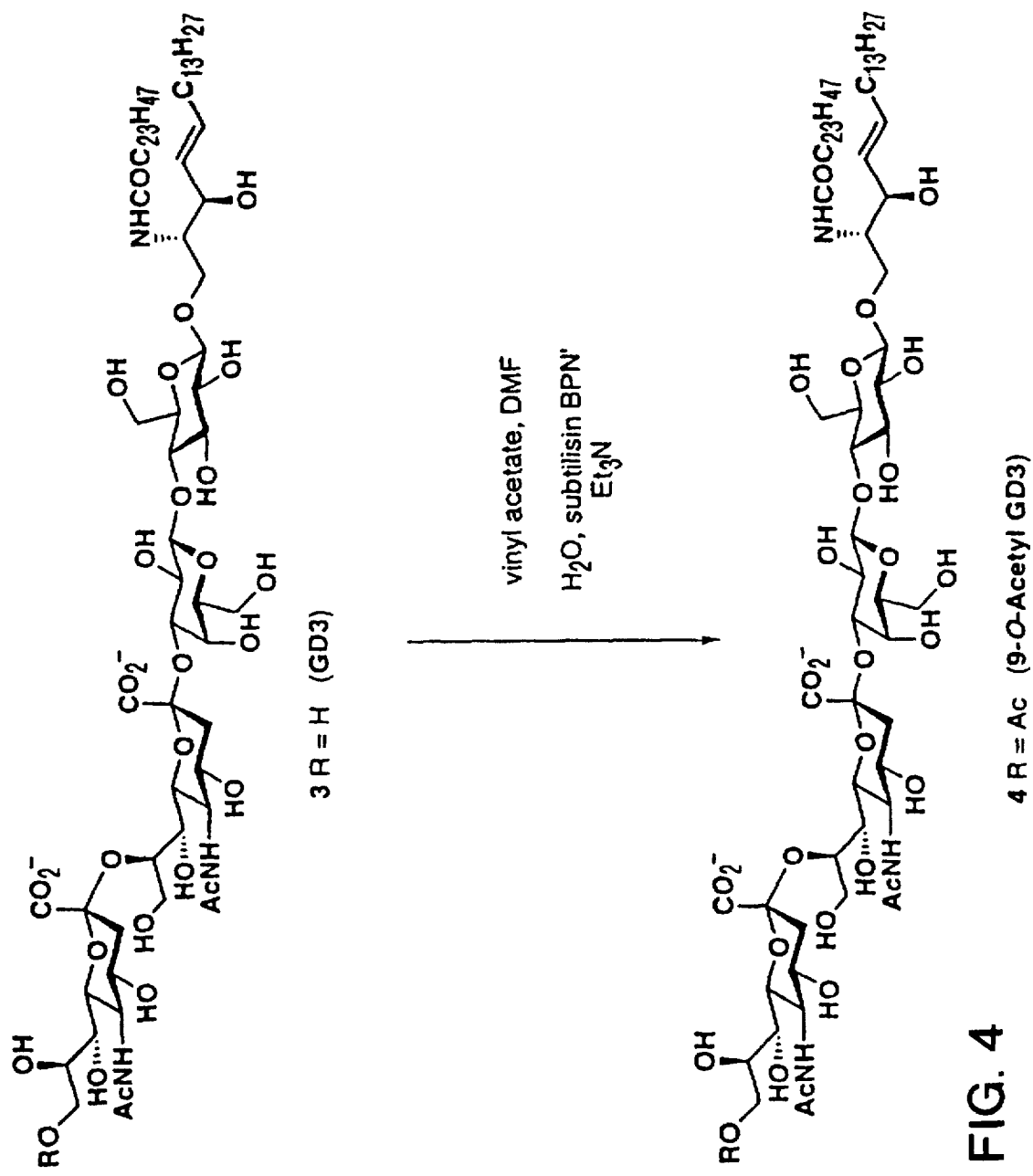

FIG. 4 illustrates enzymatic-catalyzed regioselective acetylation of GD3 (3) using subtilisin BPN' with vinyl acetate, triethylamine, in dimethylformamide (DMF) to form 9-O-acetyl-GD3 (4).

Figure 5:
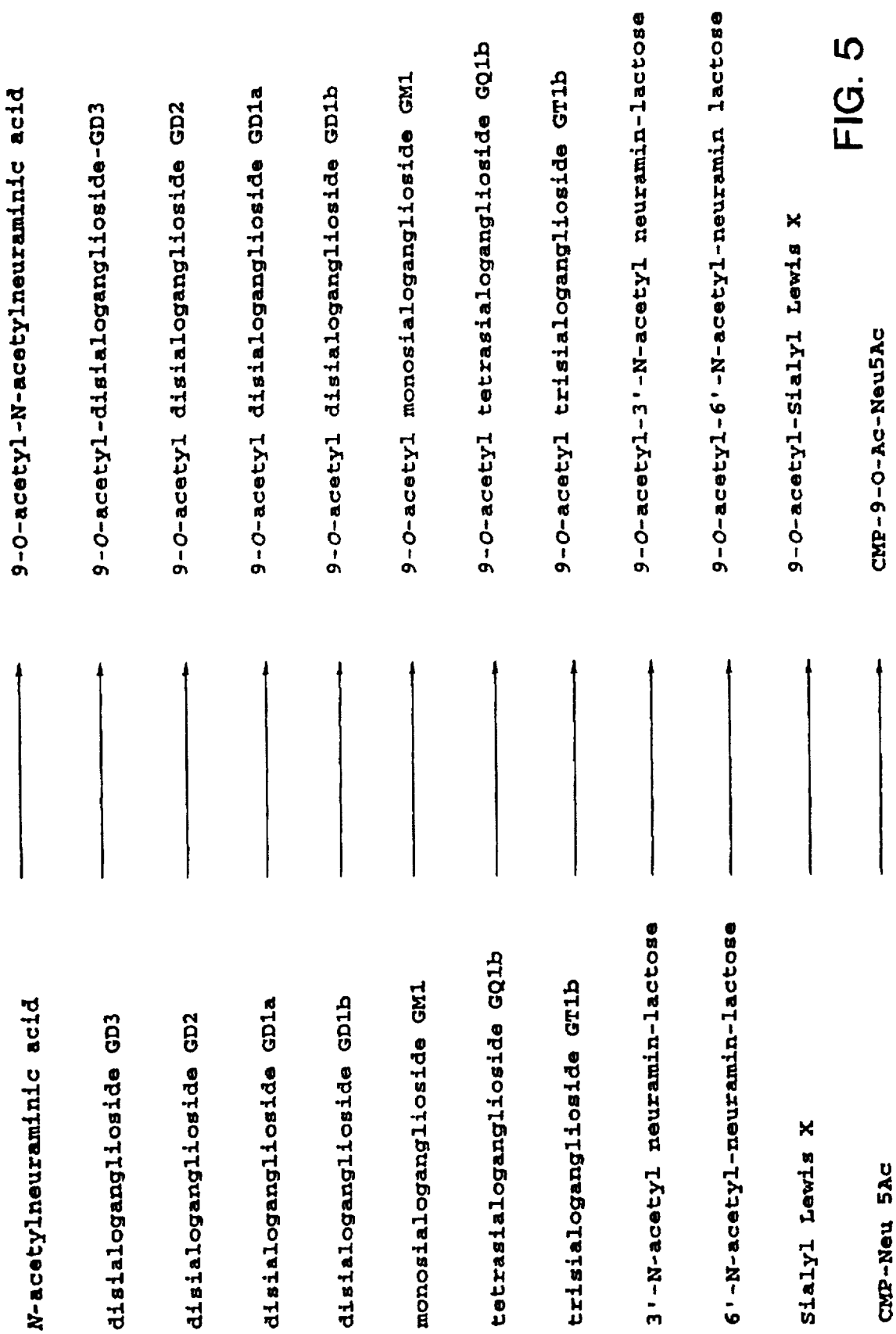

FIG. 5 illustrates a general synthesis of 9-O-Acetylneuraminic acid oligosaccharides reacting indicated neuraminic acid oligosaccharide with an acetyl donor, protease, triethylamine and organic solvent.

DETAILED DESCRIPTION OF THE INVENTION

The invention is directed to the enzymatic preparation of 9-O-acetyl N-acetylneuraminic acid functionalized oligosaccharides through regioselective enzymatic acetylation of the N-acetylneuraminic acid oligosaccharide moiety using Subtilisin and a commercially available acetate donor.

In vivo, 9-O-acetyl GD3 is produced through enzymatic acetylation of GD3 by ganglioside O-acetyl transferase(s) using acetyl-coenzyme A as the donor (Scheme 1) (Sjorberg et al. *J. Biol. Chem.* 1993, 268, 10185; Manzi et al. *J. Biol. Chem.* 1990, 265, 13091). This acetyl transferase is very labile and has not been well characterized.

An alternate enzymatic synthesis was therefore investigated for the regioselective O-acetylation of GD3 using the readily available serine protease, subtilisin BPN' and vinyl acetate as the acetate donor. Serine acylases have been very useful in regioselective acylations of carbohydrates that are difficult to perform chemically. Use of subtilisin together with DMF as the solvent has been particularly useful for acylation of oligosaccharides and other highly polar or difficult to dissolve compounds (Wong et al. *Enzymes in Organic Chemistry;* Pergamon: Oxford, 1994).

For regioselective acetylation of sugars which contain N-acetylneuraminic acid, the enzymatic acetylation of the molecule, N-acetylneuraminic acid (1), was examined since it is the terminal saccharide unit in GD3 and is itself a very important recognition element on cell surfaces. Optimal reactions were obtained in dimethylformamide (DMF) containing small amounts of water and triethyl amine at 37° C. (FIG. 3). Small amounts of water or triethyl amine were observed to increase the reaction rate of subtilisin catalyzed reactions in organic media. The added triethyl amine also neutralizes the acid functionalities on the Neu5Ac and GD3 molecules.

Next, GD3 was submitted to similar reaction conditions. A new spot appeared above GD3 on the TLC plate. After 96 hours, the reaction mixture was filtered, concentrated and chromatographed to afford pure 9-O-acetyl GD3 in 20–30% overall yield and GD3 in 55–65% overall recovered yield (FIG. 4).

The enzymatic acetylation of Neu5Ac and the disialoganglioside GD3, using Subtilisin and an acetyl donor, have thus been shown to give 9-O-acetyl Neu5Ac and 9-O-acetyl GD3, respectively. This is the first demonstration of a regioselective acetylation of GD3 at the 9-position of the terminal sialic acid moiety, as well as the first regioselective enzymatic acetylation of a disialoganglioside by a serine acylase.

Remarkably, subtilisin is able to regioselectively acetylate one hydroxyl group among the fourteen hydroxyl groups of GD3, including four which are primary, under mild conditions. This method provides access to O-acylated disialogangliosides as well as other N-acetyl-neuraminic acid oligosaccharides which are biologically and medicinally important and are difficult to obtain from nature or by chemical acylations. Examples of other N-acetyl-neuraminic acid oligosaccharides include N-acetylneuraminic acid, disialoganglioside GD3, disialoganglioside GD2, disialoganglioside GD1a, disialoganglioside GD1b, monosialoganglioside GM1, tetrasialoganglioside GQ1b, trisialoganglioside GT1b, 3'-N-acetyl-neuramin-lactose, 6'-N-acetyl-neuramin-lactose, Sialyl Lewis X and CMP-Neu 5Ac.

9-O-Acetyl GD3, synthesized as indicated above, may be dissolved in a sterile physiological saline buffer for injection and employed as an immunogenic agent for raising anti-GD-3 antibodies. Anti-GD-3 antibodies are useful as diagnostic agents for detecting melanoma cells. Anti-GD-3 antibodies may also be administered to melanoma patients as a passive immunotherpeutic. 9-O-Acetyl GD3 may also be employed as a vaccine. When administered to healthy patients, 9-O-acetyl GD3 elicits an immune response which provides resistance to the development of melanoma. When administered to melanoma patients, 9-O-acetyl GD3 elicits an immune response which provides a therapeutic anti-GD-3 response.

SYNTHETIC PROTOCOLS

General

A Bruker AMX-400 (TM) spectrometer was used for 400 MHZ $^1$H NMR and 100 MHZ $^{13}$C NMR spectra. High resolution mass spectra (HRMS) were obtained on a VG ZAB-ZSE Mass Spectrometer (TM) in fast atom bombardment. For the MS of the compounds that are obtained from the MCC, normal molecular ion peaks (M+H$^+$, M+Na$^+$ or M+Cs$^+$) were recorded without high resolution.

Water was distilled from Milli-Q water system in Millipore (TM). Chemicals and solvents were reagent grade and were used without further purification. N-Acetylneuraminic acid (1) and GD3 (3) are available from Sigma (TM). Ion-exchange resin (Dowex (TM) 1×8, Cl$^-$ from, 100–200 mesh) was obtained from Sigma. Biogel P-2 was obtained from Sigma. Silica gel was obtained from Merck (TM) and analytical thin-layer chromatography was performed with pre-coated Merck (TM) silica gel type 60, $F_{254}$.

The enzymes were obtained from Sigma: subtilisin BPN', subtilisin Carlsberg. Commercial enzymes were not assayed; the reported activities refer to the activities stated by Sigma (TM).

Synthesis of 9-O-Acetyl Neu5Ac (2) as illustrated in figure 3:

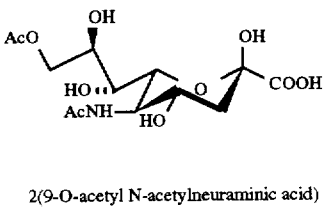

2(9-O-acetyl N-acetylneuraminic acid)

A mixture of N-acetylneuraminic acid (1) (30 mg, 0.10 mmol; Sigma), dimethylformamide (DMF) (0.27 mL), vinyl acetate (0.16 mL), 0.1M pH 8.0 potassium phosphate buffer (0.01 mL), triethyl amine (0.012 mL), and Subtilisin BPN' (2×10 mg , 200 U total, 10 mg at the beginning and after 24 hours; Sigma) was stirred at 37° C. for 48 hours. The reaction was stopped by adding methanol and filtering through celite. The residue was adsorbed onto silica gel and chromatographed ($SiO_2$, EtOAc/MeOH/0.02% $CaCl_2$ aq, 5/2/1) to afford the title compound (25 mg, 73%).

EtOAc. The organic layer is washed with $H_2O$, sat. $NaHCO_3$, $H_2O$, 1N HCl, $H_2O$ and brine, dried over $MgSO_4$, and concentrated in vacuo. The residue is distilled (bp 96° C./4 mmHg) to give the desired cyanomethyl acetate donor. For other example of cyanomethyl ester synthesis, see: Wong, C.-H. *J. Am. Chem. Soc.* 1990, 112, 5313.

General Synthesis of 9-O-Acetylneuraminic acid oligosaccharides as illustrated in FIG. 5:

A mixture of N-acetylneuraminic acid functionalized oligosaccharide (0.0018 mmol) selected from the group consisting of N-acetylneuraminic acid (Sigma; CAS # 131-48-6), disialoganglioside GD3 (Sigma; CAS # 62010-37-1), disialoganglioside GD2 (Sigma; CAS # 65988-71-8), disialoganglioside GD1a (Sigma; CAS # 12707-58-3), disialoganglioside GD1b (Sigma # G8146), monosialoganglioside GM1 (Sigma; CAS # 37758-47-7), tetrasialoganglioside GQ1b (Sigma; CAS # 68652-37-9), trisialoganglioside GT1b (Sigma; CAS # 59247-13-1), 3'-N-acetyl-neuraminlactose (Sigma; CAS # 35890-38-1), 6'-N-acetyl-neuraminlactose (Sigma; CAS # 74609-39-5), Sialyl Lewis X (J. Am. Chem Soc. 1992, 114, 9283) and CMP-Neu 5Ac (Sigma), organic solvent selected from the group consisting of Synthesis of 9-O-Acetyl Neu5Ac (2) as illustrated in figure 3:

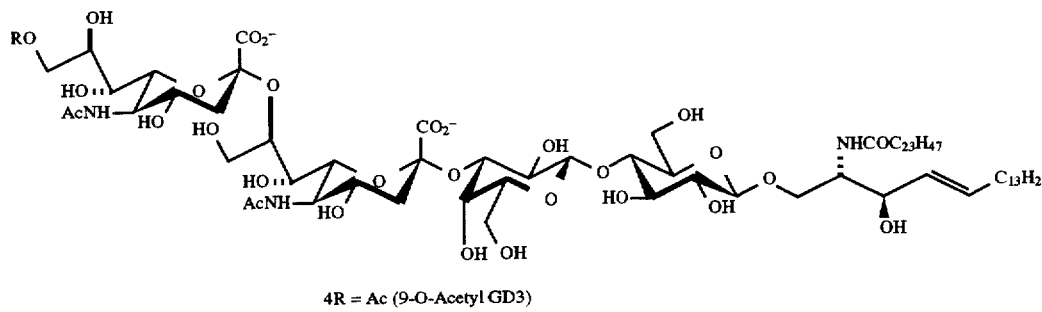

4R = Ac (9-O-Acetyl GD3)

A mixture of $GD_3$ (3) (3 mg, 0.0018 mmol; Sigma), dimethylformamide (DMF) (0.058 mL), vinyl acetate (0.039 mL), 0.1M pH 8.0 potassium phosphate buffer (0.002 mL), triethyl amine (0.80 μL), and Subtilisin BPN' (4×1 mg, 40 U total, 1 mg portions added at 0 hours, 24 hours, 48 hours, 72 h) was stirred at 37° C. for 96 hours. The reaction was stopped by adding methanol and filtering through celite. The residue was adsorbed onto silica gel (20 mg) and chromatographed ($SiO_2$, EtOAc/MeOH/0.02% $CaCl_2$ aq, 5/2/1) to afford the title compound (0.7 mg, 23%) and recovered $GD_3$ (1.9 mg, 63%)

General Synthesis of Acetate donors: trifluoroethyl acetate, trichloroethyl acetate, acetone oxime acetate and others:

A mixture of acetyl chloride (1 mol) and either one of the following: an alcohol, thiol or oxime (1 mol; e.g. trifluoroethanol; trichloroethanol; acetone oxime; methyl alcohol; ethanol; benzyl alcohol; cyclohexanone oxime; cyclopentanone oxime; ethane thiol; cyclohexyl mercaptan; cyclohexyl mercaptan, etc.) in 0.10M pyridine is stirred at 25° C. for 12 hours. The mixture is then cooled and dissolved in EtOAc. The organic layer is washed with $H_2O$, dil $H_2SO_4$, sat. $NaHCO_3$, $H_2O$ and brine, dried over $MgSO_4$, and concentrated in vacuo. The residue is distilled to give the desired acetate donor.

General Synthesis of Acetate donors: Cyanomethyl acetate donors:

A mixture of acetic acid (50 mmol), triethylamine (75 mmol) and chloroacetonitrile (150 mmol) are stirred at 70° C. for 4 hours. The mixture is then cooled and dissolved in dimethylformamide, t-butanol, 1-pentanol, tetrahydrofuran, dioxanes, pyridine, toluene, acetone, diethyl ether, diisopropyl ether, ditertbutyl ether, chloroform, benzene, methylene chloride and mixtures of said organic solvents (0.031 Molar total), acetate donor selected from the group consisting of vinyl acetate, isopropenyl acetate, trifluoroethyl acetate, trichloroethyl acetate, cyanomethyl acetate and acetoxime acetate (0.423 mmoles; synthesized supra), 0.1M pH 8.0 potassium phosphate buffer (0.002 mL; alternatively purified water can be used in lieu of buffer), triethyl amine (5.74 μmoles), and protease selected from the group consisting of Subtilisin BPN', Subtilisin Carlsberg, Subtilisin 8350, Subtilisin 8397 and protease N (4 X, 40 U total, needed portions added at 0 hours, 24 hours, 48 hours, 72 hours; Sigma) is stirred at 37° C. for 96 hours. The reaction is stopped by adding methanol (ethanol, etc.) and filtering through celite. The residue is adsorbed onto silica gel (approx. 20 mg) and chromatographed ($SiO_2$, approximately EtOAc/MeOH/ 0.02% $CaCl_2$ aq, 5/2/1) to afford the title compound.

What is claimed is:

1. An enzymatic process for regioselectively acetylating an N-acetylneuraminic acid functionalized oligosaccharide comprising the following step:

Step A: Reacting the N-acetylneuraminic acid functionalized oligosaccharide with an acetyl donor in an organic solvent in the presence of a protease for producing an 9-O-acetyl N-acetylneuraminic acid functionalized oligosaccharide and in the presence of triethyl amine for increasing the reaction rate and neutralizing acid functionalities on the 9-O-acetyl N-acetylneuraminic acid functionalized oligosaccharide.

2. The process as described in claim 1 wherein the N-acetylneuraminic acid functionalized oligosaccharide is selected from the group consisting of N-acetylneuraminic acid, disialoganglioside GD3, disialoganglioside GD2, disialoganglioside GD1a, disialoganglioside GD1b, monosialoganglioside GM1, tetrasialoganglioside GQ1b, trisialoganglioside GT1b, 3'-N-acetyl-neuramin-lactose, 6'-N-acetyl-neuramin-lactose, Sialyl Lewis X and CMP-Neu 5Ac.

3. The process as described in claim 2 wherein the protease is selected from the group consisting of Subtilisin BPN', Subtilisin Carlsberg, Subtilisin 8350, Subtilisin 8397 and protease N.

4. The process as described in claim 3 wherein the acetyl donor is selected from the group consisting of vinyl acetate, isopropenyl acetate, trifluoroethyl acetate, trichloroethyl acetate, cyanomethyl acetate and acetoxime acetate.

5. The process as described in claim 4 wherein the 9-O-acetyl N-acetylneuraminic acid functionalized oligosaccharide is selected from the group consisting of 9-O-acetyl-N-acetylneuraminic acid, 9-O-acetyl-disialoganglioside-GD3, 9-O-acetyl-disialoganglioside GD2, 9-O-acetyl-disialoganglioside GD1a, 9-O-acetyl-disialoganglioside GD1b, 9-O-acetyl-monosialoganglioside GM1, 9-O-acetyl-tetrasialoganglioside GQ1b, 9-O-acetyl-trisialoganglioside GT1b, 9-O-acetyl-3'-N-acetyl-neuramin-lactose, 9-O-acetyl-6'-N-acetyl-neuramin-lactose, 9-O-acetyl-Sialyl Lewis X and CMP-9-O-Ac-Neu 5Ac.

6. The process as described in claim 5 wherein the organic solvent is selected from the group consisting of dimethylformamide, t-butanol, 1-pentanol, tetrahydrofuran, dioxanes, pyridine, benzene, toluene, acetone, diethyl ether, diisopropyl ether, ditertbutyl ether, chloroform, methylene chloride and mixtures of chloroform and methylene chloride with a solvent selected from the group consisting of dimethylformamide, t-butanol, 1-pentanol, tetrahydrofuran, dioxanes, pyridine, toluene, acetone, diethyl ether, diisopropyl ether, ditertbutyl ether.

7. The process as described in claim 1 wherein:

the N-acetylneuraminic acid functionalized oligosaccharide is N-acetylneuraminic acid, the protease is Subtilisin BPN', the acetyl donor is vinyl acetate, the organic solvent is dimethylformamide, and the 9-O-acetyl N-acetylneuraminic acid functionalized oligosaccharide is 9-O-acetyl N-acetylneuraminic acid.

8. The process as described in claim 1 wherein the N-acetylneuraminic acid functionalized oligosaccharide is GD3, the protease is Subtilisin BPN', the acetyl donor is vinyl acetate, the organic solvent is dimethylformamide, and the 9-O-acetyl N-acetylneuraminic acid functionalized oligosaccharide is 9-O-acetyl GD3.

\* \* \* \* \*